(12) United States Patent
Geczy (10) Patent No.: US 7,671,042 B2
(45) Date of Patent: Mar. 2, 2010

(54) PHARMACEUTICAL COMPOSITIONS CONTAINING CYCLODEXTRINS AND TAXOIDS

(76) Inventor: Joseph M. Geczy, Avenue Wolvendael 21/6, Brussels (BE) B-1180

( * ) Notice: Subject to any disclaimer, the term of this patent is extended or adjusted under 35 U.S.C. 154(b) by 421 days.

(21) Appl. No.: 11/542,797

(22) Filed: Oct. 4, 2006

(65) Prior Publication Data

US 2007/0087999 A1    Apr. 19, 2007

Related U.S. Application Data

(63) Continuation of application No. 09/554,064, filed as application No. PCT/HU98/00097 on Nov. 9, 1998, now abandoned.

(30) Foreign Application Priority Data

Nov. 10, 1997    (HU) ..................... 9701945

(51) Int. Cl.
*A61K 31/337* (2006.01)
*A61K 31/724* (2006.01)
(52) U.S. Cl. ........................ 514/58; 514/449
(58) Field of Classification Search ............... None
See application file for complete search history.

(56) References Cited

U.S. PATENT DOCUMENTS 5,654,422 A * 8/1997 Hirsenkorn ............... 536/103
6,858,644 B2 * 2/2005 Benigni et al. ............ 514/449

FOREIGN PATENT DOCUMENTS

EP          717041    *  6/1996
WO     WO 96/14872    *  5/1996

OTHER PUBLICATIONS

Vippagunta, S. et al "Crystalline Solids" Adv. Drug Delivery Rev. (2001) vol. 48, pp. 3-26.*

* cited by examiner

*Primary Examiner*—Leigh C Maier
(74) *Attorney, Agent, or Firm*—Pearl Cohen Zedek Latzer, LLP (57) ABSTRACT

The present invention relates to water-soluble solid pharmaceutical compositions and their solutions in aqueous solvents, said compositions containing a) as an active ingredient a finely dispersed large surface area amorphous preferably lyophilized taxoid such as paclitaxel or docetaxel, their salts or their polymorphic hydrates or solvates such as solvates formed with ethanol and b) finely dispersed large surface area amorphous preferably lyophilized acetyl-γ-cyclodextrin or hydroxy-propyl-β-cyclodextrin (cyclodextrin) whereby the weight ratio of said taxoid:said cyclodextrin ranges between 1:25 and 1:400; c) and optionally other water-soluble auxiliary materials usual in pharmaceuticals for parental purposes.

7 Claims, 6 Drawing Sheets

PHARMACEUTICAL COMPOSITIONS CONTAINING CYCLODEXTRINS AND TAXOIDS

This application is a continuation of U.S. patent application Ser. No. 09/554,064, filed Jul. 18, 2000, which is a national phase application of PCT/HU98/00097, filed on Nov. 9, 1998, claiming priority to Hungarian patent application No. P97 01945, filed Nov. 10, 1997, the disclosures of which are hereby incorporated by reference in their entirety.

This invention relates to new water-soluble solid pharmaceutical compositions and their aqueous solutions for parenteral use containing taxoids and certain cyclodextrins without noxious solvents and/or detergents. More particularly the invention relates to new water-soluble solid pharmaceutical compositions and their solutions in aqueous solvents, said compositions containing a) as an active ingredient a taxoid such as paclitaxel and docetaxel, optionally in the form of their salts or their polymorphic hydrates or solvates e.g. solvates formed with ethanol; and b) a large surface area acetyl-γ-cyclodextrin or hydroxypropyl-β-cyclodextrin (in the following the cyclodextrin) whereby the weight ratio of said taxoid to said cyclodextrin ranges between 1:25 and 1:250;

c) and optionally other water-soluble auxiliary materials usual in pharmaceuticals for parenteral purposes.

The invention also relates to the preparation and use of said injectable pharmaceutical compositions.

The following definitions are used throughout the specification and claims:

paclitaxel=taxol A;
docetaxel=(N-debenzoyl-N-tert.-butoxycarbonyl)-10-deacetyl-paclitaxel;
"aqueous solvents"=water of injectable quality or an aqueous solution containing a dissolved isotonizer in an amount and concentration effective to isotonize said aqueous solution e.g. sodium chloride, glucose;
"amorphised"=showing amorphous structure against X-rays;
CD=cyclodextrin
γ-cyclodextrin=cyclomaltooctaose
β-cyclodextrin=cyclomaltoheptaose
AcγCD=acetyl-γ-cyclodextrin
HPβCD=hydroxypropyl-β-cyclodextrin (about 2 to about 8 hydroxypropyl groups per CD-unit)
DIMEβ=heptakis-2,6-di-0-methyl-β-cyclodextrin Taxoid is the collective name for paclitaxel and structurally related substances. Paclitaxel is a compound known for its significant anticancer activity acting as a mitotic spindle poison and as a potent inhibitor of cell replication. It also is known to have poor aqueous solubility of about 0.0005 mg/ml at ambient temperature and is reported to be unstable both in solution upon storage and as a consequence of solvolysis of its ester linkage leading to loss of cytotoxic activity. It is marketed in solution of a 1:1 mixture of ethanol and Cremophor EL (polyhydroxylated castor oil).

Cremophor EL has been implicated in some adverse reactions (hypersensitivity, histamine release) during intravenous treatment and therefore many attempts have been made in the past decade to develop new drug delivery systems.

When paclitaxel is formulated as a solution in the organic solvents ethanol and polyethoxylated castor oil, it is administered as a supersaturated oil-in-water emulsion and dilutes rapidly in the blood, an aqueous environment rich in hydrophobic domains provided by lipids and proteins. Paclitaxel passes through the hydrophobic environment of the plasma membrane while entering and leaving cells by diffusion.

The propensity of paclitaxel to undergo solvent- and concentration-dependent self-aggregation has hampered efforts to formulate this poorly soluble drug in pharmaceutically acceptable excipients for clinical administration.

It is also known that docetaxel, a semisynthetic taxoid is highly lipophylic and more water soluble than paclitaxel [U.S. Pat. No. 4,814,470]. Commercially available docetaxel for injection concentrates is a sterile solution of the drug in polysorbate 80, with an accompanying diluent of 13% (w/w) ethanol in water for injection. The maximal drug concentration which could be used was 0.3 to 0.9 mg/ml. Higher than 0.9 mg/ml had to be avoided because of precipitation problems. Hypersensitivity reactions associated with polysorbate 80 might cause problems with commercially available formulations A wide range of approaches has been taken in formulation, including vehicles with hydrophobic characteristics. In most vehicles the taxoid is formulated in the millimolar concentration range which is comparable to the concentrations at which the taxoid was observed to self-aggregate resulting in precipitation.

Based on the interaction between the taxoid and cyclodextrins several further suggestions were made. Studying the thin-layer chromatographic mobility of the taxoid in presence of cyclodextrins (Int. J. Pharm. 1994. 108. 64-75. ) it was first concluded that the interaction between taxoid and cyclodextrin was very weak. Later (AU-P-35544/93; 645.927) a modest enhancement of the solubility of the taxoid was found using unsubstituted cyclodextrins and enzyme-modified branched-β-cyclodextrins.

Aqueous parenteral solutions of sparingly soluble drugs in water combined with cyclodextrins were suggested to minimize drug precipitation at injection sites or organs following parenteral application (U.S. Pat. No. 5,024,998). Solubility enhancement was hereby observed using high (around 50% w/v) CD concentration and solid complexes were obtained with some products from these concentrates emphasizing that below a 20% w/v CD concentration precipitation might occur. Among the tremendous amount of drugs enlisted in this specification there is no word concerning taxoids nor acetyl-γCD.

Using an aqueous solution of methylated β-cyclodextrins as effective paclitaxel solubility enhancers (PCT WO 94/26728) and combining of methylated β-cyclodextrin and ethanol for preparation of 1 to 4 mg/ml paclitaxel solutions (EP 788373) represented further improvements. These taxoid concentrates did not precipitate on dilution up to a certain limit and avoided use of toxic detergents. Also the use of 2,6-di-O-methyl-β-cyclodextrin was suggested as a more effective solubilizer of paclitaxel (EPA 0639380) and detailed results on its solubilizing potency were published (J. Pharm. Sci. 84. 10. 1223-1230; 1995). However some concern was expressed concerning the use of methylated β-cyclodextrins in injectables because of their surfactant properties, their affinity to cholesterol and other cell-membrane lipid components already at low concentration and doses.

Some studies were published on the use of cyclodextrins along with water-soluble drugs to achieve less ulceration compared in the same formulation of cytotoxic compounds when extravasated (WO 95/06485). Though paclitaxel is not water-soluble, this patent specification also includes an example of "Taxol" in 50% ethanol solution to illustrate this effect adding "HPCD". The results show that HPCD exerted a protective effect on skin when Taxol was deposited into an intradermal site, resulting in the reduction in lesion size.

Thio-branched cyclodextrins were disclosed for solubilizing anticancer taxoids (e.g. docetaxel and paclitaxel see PCT WO 95/19994) without details concerning improvement of solubility, stability or toxicity. Such formulations provided a significant increase of aqueous solubility for paclitaxel. However on dilution for parenteral application (0.3 to 1.2 mg/ml) precipitation of the drug occured.

It was the aim of the present invention to further improve both solubility of taxoids in injectable formulations and stability of taxoid drug systems for parenteral administration while possibly decreasing toxicity of accompanying materials used for formulation purposes.

The basis of the present invention is the recognition that both acetylated-γ-cyclodextrin and hydroxy-propyl-β-cyclodextrin exhibit a positive effect on the prolongation of the oversaturated state of dissolved paclitaxel and docetaxel preventing premature precipitation without using ethanol as a co-solvent. This was a surprising fact it being known that γ-cyclodextrin and its hydroxypropylated derivatives—which are known to possess the largest size cavities among the CDs—have been previously disclosed to be less suitable for paclitaxel solubilization and complexation (Int. J. Pharm. 133. 191-201.1996). This was confirmed by our studies registering the equilibrium solubility of paclitaxel in function of the concentration of aqueous solutions of chemically modified γ-cyclodextrins whereby no practically useful solubilizing effect was found though high cyclodextrin-concentrations were used. See Table 1: Solubility of paclitaxel as a function of acetyl-γ-cyclodextrin concentration).

TABLE 1

| Acetyl-γ-cyclodextrin (%) w/v | Dissolved Paclitaxel (μg/ml) |
|---|---|
| 2 | 4.0 |
| 5 | 8.8 |
| 10 | 25.0 |
| 20 | 48.0 |
| 40 | 170.0 |

The aqueous solubility of paclitaxel at room temperature is about 0.5 μg/ml, therefore the 170 μg/ml dissolved paclitaxel concentration achieved in 40% acetyl-γ-cyclodextrin solution already means an about 340-fold solubility enhancement. The above data however are poor as compared with the known results according to which in an aqueous 40% w/v solution of DIMEβ about 800-1000 μg/ml of paclitaxel was dissolved. Similar poor results were found using HPβCD as a solubilizer. This value is far from the desirable value corresponding to the therapeutic dose of paclitaxel and the use of such dosage form would require administration of more than 70 grams of cyclodextritn with the paclitaxel dose unit of 30 mg.

The object of the present invention is a process for the preparation of pharmaceutical compositions for parenteral use in instantly water-soluble solid state as well as the solutions thereof in aqueous solvents containing acetyl-γ-cyclodextrin or hydroxy-propyl-β-cyclodextrin (in the following named cyclodextrin) comprising a) dissolving a taxoid preferably paclitaxel or docetaxel, or their salts or hydrates in ethanol and thereafter performing either of the following steps:
   i) adding the solid cyclodextrin and optionally other water-soluble auxiliary materials usual in pharmaceuticals for parenteral purposes, dissolving the mixture in an aqueous solvent and lyophilising to obtain a solid or
   ii) adding the solid, large surface area amorphous (preferably lyophilised) cyclodextrin and optionally other water-soluble auxiliary materials usual in pharmaceuticals for parenteral purposes, evaporating the solvent and drying to obtain a solid or
   iii) admixing the solution with solid large surface area amorphous preferably freeze-dried cyclodextrin (and optionally other water-soluble auxiliary materials usual in pharmaceuticals for parenteral purposes), thereafter dissolving with an aqueous solvent optionally in the presence of an effective amount of an isotonizing additive to obtain a solution;

containing
a) as an active ingredient the said taxoid and
b) the said cyclodextrin and
c) optionally other water-soluble auxiliary materials usual in pharmaceuticals for parenteral purposes whereby the weight ratio of taxoid:cyclodextrin is between the range 1:25 to 1:400; and optionally b) when steps i) or ii) were used dissolving the solid in an aqueous solvent to obtain a parenteral solution ready for direct medical treatment.

According to the invention the taxoid paclitaxel is used in its hydrated polymorphic form or in its solvated form such as the ethanol solvate.

It is a preferred embodiment of the invention to use as the active ingredient paclitaxel together with acetyl-γ-cyclodextrin in a 1:100 to 1:250 weight ratio. Another preferred embodiment is the use of docetaxel with HPβCD in the range of 1:25 to 1:100 weight ratio.

When carrying out the process according to the invention any of the following can be used as the aqueous solvent or diluent: water of injectable quality, an aqueous solution of an isotonizing additive such as sodium chloride, glucose, mannitol, dextrose. The latter solutions have to contain said ingredients in an amount to effectively isotonize the aqueous solution under the conditions hereunder. Thus the concentrations known to be suitable for isotonizers in pharmaceutical solutions might be changed somewhat by the presence of the cyclodextrins and the taxoids employed. Thus the concentrations in the magnitude of about 0.9% w/v of sodium chloride, or about 5% w/v of glucose have to be optimised for the specific composition depending on the taxoid employed and on the amount and quality of the CD used.

Further objects of the present invention are the pharmaceutical compositions containing as active ingredients any of the products whenever prepared according to the processes of the invention.

A still further object of the present invention are water-soluble solid pharmaceutical compositions and their solutions in aqueous solvents, said compositions containing a) as an active ingredient a finely dispersed large surface area taxoid such as paclitaxel or docetaxel, optionally in the form of their salts or their polymorphic hydrates or solvates e.g. formed with ethanol and
b) finely dispersed, large surface area acetyl-γ-cyclodextrin or hydroxy-propyl-β-cyclodextrin (cyclodextrin) the weight ratio of said taxoid:said cyclodextrin ranging between 1:25 and 1:250;
c) and optionally other water-soluble auxiliary materials usual in pharmaceuticals for parenteral purposes.

Preferred compositions according to the invention contain as the active ingredient paclitaxel and as the cyclodextrin acetyl-γ-cyclodextrin in a 1:100 to 1:250 weight ratio. Further preferred compositions are combinations of docetaxel and hydroxy-propyl-β-cyclodextrin in a 1:25 to 1:100 weight ratio.

Further objects of the present invention are methods for prevention of self-aggregation and premature precipitation of a taxoid such as paclitaxel and docetaxel and their salts, solvates and hydrates in aqueous solutions and for prolongation of the oversaturated dissolved state of the drugs by using the taxoids in the form of pharmaceutical compositions according to the present invention as described above in detail.

Yet another object of the present invention is the method of treatment of unwanted cell proliferation by utilising effective amounts of pharmaceutical compositions according to the invention as described above in detail. The ready-to-use paclitaxel solutions remain physically stable for a reasonable period of time. Intravenous treatment generally requires that solutions be used which are physically stable for at least 6 hours. When dissolving the compounds according to the present invention in aqueous solutions the thus reconstituted solutions are stable for at least 6 to 8 hours. In the case of solutions of the combinations paclitaxel/AcγCD as well as docetaxel/AcγCD or HPβCD more than 24 hours of physical stabilities were measured.

According to the method it is provided to administer to a patient in need of such treatment a parenteral dosage form containing the pharmaceutical composition. Dosage units of 100 mg taxoid may be prepared in lyophilised form. These are diluted to give the ready to use dosage solutions applicable e.g. for intravenous treatment. Depending on the required treatment applicable in the specific needs of the patient several 100 mg units may be applied so as to reach the effective dose corresponding to the desired amount expressed generally in mg/m$^2$ body surface. Thus e.g. the recommended dose of paclitaxel ranging from 135 to 250 mg/m$^2$ body surface can be reached. The drug can be used effectively e.g. by way of intravenous, intraperitoneal, intramuscular administration depending on the type of cancer to be treated and the taxoid and cyclodextrin selected for use. Improved results of treatment as compared with known therapies can be achieved due to the considerably decreased toxicity of the dosage form as compared with the toxicity of the vehicles contained in the known compositions used to date. It is also no more necessary to subject the patient to premedication against hypersensitivity and other unwanted side-effects using steroids, antihistamines and H$_2$-receptor antagonists before paclitaxel or docetaxel administration to prevent severe hypersensitivity reactions.

Details of the invention are given in the Examples below by way of illustration and without the intention to limit the scope of protection.

I. PREPARATION OF FORMULATIONS

Example I.1.

Preparation of Reconstitutable, Solid paclitaxel/acetyl-γ-cyclodextrin Combinations by Drying 3 mg of paclitaxel (dissolved in 0.3 ml of ethanol) are added to 500 mg of acetyl-γ-cyclodextrin powder (freeze-dried from aqueous solution). This mixture is kept under vacuum for 18 hours over phosphorous pentoxide to remove the ethanol. Portions of this ethanol-free powder combination are dissolved in 5, 4, 3 and 2 ml of 5% aqueous glucose solutions respectively. The physical stability of these reconstituted solutions is shown in Table 2.

TABLE 2

|  | Added ml of 5% glucose solution | | | |
| --- | --- | --- | --- | --- |
|  | 5 ml | 4 ml | 3 ml | 2 ml |
| final paclitaxel mg/ml | 0.6 | 0.75 | 1.0 | 1.5 |
| final Ac γCD mg/ml | 100 | 125 | 167 | 250 |
| stability evaluated visually in hours. | >120 | >48 | >48 | >48 |
|  |  | after 72 hours precipitation occurred | | |
| dissolved paclitaxel mg/ml (HPLC) | 0.576 | | | |

This experiment has been repeated with lower amounts of acetyl-γ-cyclodextrin. 3 mg of paclitaxel (dissolved in 0.3 ml of ethanol) is added to 450 mg, 400 mg or 350 mg of freeze-dried acetyl-γ-cyclodextrin samples, thereafter it is kept under vacuum for 18 hours over phosphorous pentoxide to remove the ethanol.

These combinations have been dissolved in 5, 4, 3 and 2 ml each of an 5% aqueous glucose solution. In Table 3, 4, 5 the composition as well as the physical stability of these reconstituted paclitaxel solutions prepared according to Example I.1 using different amounts of acetyl-γ-cyclodextrin are summarised.

TABLE 3

|  | Added ml of 5% glucose solution | | | |
| --- | --- | --- | --- | --- |
|  | 5 ml | 4 ml | 3 ml | 2 ml |
| final paclitaxel mg/ml | 0.6 | 0.75 | 1.0 | 1.5 |
| final acetyl-γ-cyclodextrin | 90 | 112.5 | 150 | 225 |
| stability, evaluated visually in hours. | opalescent solution | >48 | >48 | >48 |

TABLE 4

| | Added ml of 5% glucose solution | | | |
|---|---|---|---|---|
| | 5 ml | 4 ml | 3 ml | 2 ml |
| final paclitaxel mg/ml | 0.6 | 0.75 | 1.0 | 1.5 |
| final acetyl γCD mg/ml | 80 | 100 | 133 | 200 |
| stability, evaluated visually in hours. | <4 slight opalescence | | | >24 clear solution |
| dissolved paclitaxel mg/ml | | | | |
| on prep. | 0.41 | | | 1.26 |
| after 22 hours. | 0.42 | | | 1.25 |

TABLE 5

| | Added ml of 5% glucose solution | | | |
|---|---|---|---|---|
| | 5 ml | 4 ml | 3 ml | 2 ml |
| final paclitaxel mg/ml | 0.6 | 0.75 | 1.0 | 1.5 |
| final Ac γCD | 70 | 86 | 117 | 175 |
| stability, evaluated visually in hours. | | increasing opalescence | increasing opalescence | >24 almost clear solution |
| dissolved paclitaxel mg/ml (HPLC) | | | | |
| at prep. | | | | 1.16 |
| after 22 hours. | | | | 1.17 |

Example I.2.

Preparation of a paclitaxel Formulation of 0.6 mg/ml Nominal paclitaxel Concentration 6.5 g of amorphised acetyl-γ-cyclodextrin are wetted with 3 ml of a paclitaxel solution of 10 mg/ml paclitaxel concentration (corresponding to 30 mg of paclitaxel). Immediately 50 ml of a 5% dextrose solution are added to the wet mixture and the composition is shaken until a clear solution is obtained. The dissolved paclitaxel concentration in solution amounts to 0.55±0.05 mg/ml determined by HPLC after filtration of the solution through a 0.2 μm membrane filter. The solution can be stored at room temperature under normal light conditions in glass containers for at least 6 hours without noticeable opalescence and/or particle formation. The re-analysis of the dissolved paclitaxel after 6 hours of storage by HPLC shows that no decrease of dissolved paclitaxel concentration took place.

Example I.3.

Preparation of a paclitaxel Formulation of ~0.3 mg/ml Nominal paclitaxel Concentration 6.5 g of previously amorphised acetyl-γ-cyclodextrin is wetted with 3 ml of a paclitaxel solution of 10 mg/ml paclitaxel concentration (corresponding to 30 mg of paclitaxel). To this wet mixture immediately 100 ml of a 5% dextrose solution are added and the mixture is shaken until a clear solution is obtained. The dissolved paclitaxel concentration in this solution amounts to 0.27±0.03 mg/ml, determined by HPLC after filtration of the solution across a 0.2 μm membrane filter. The solution can be stored at room temperature under normal light conditions in glass containers for at least 12 hours without noticeable opalescence and/or particle formation. The HPLC re-analysis of the dissolved paclitaxel after 12 hours of storage shows that no decrease of dissolved paclitaxel concentration took place during 12 hours.

Example I.4.

Preparation of docetaxel Formulation of 0.5 and 1 mg/ml Nominal docetaxel Concentration 100 mg of amorphised acetyl-γ-cyclodextrin are wetted with 0.1 ml of a docetaxel solution of 20 mg/ml docetaxel concentration (this corresponds to 2 mg of docetaxel). To samples of this wet solid mixture immediately 1 or 2 ml of a 5% w/v aqueous dextrose solution are added and the mixture is shaken until a clear solution is obtained. The dissolved docetaxel concentrations in solution according to Example I.4. amount to 1 and 0.5 mg/ml respectively. The solutions can be stored at room temperature under normal light conditions in glass containers for at least 24 hours without noticeable opalescence and/or particle formation. The composition of both solutions referred to 20 mg docetaxel dosage unit is as follows:
1000 mg AcγCD
20 mg docetaxel
1 ml ethanol
20 ml or 40 ml 5% dextrose Example I.5.

Preparation of a docetaxel Formulation of 0.75 mg/ml Nominal docetaxel Concentration Using hydroxypropyl-β-cyclodextrin (HPβCD)

200 mg of HPβCD is wetted with 0.15 ml of a docetaxel solution of 10 mg/ml docetaxel concentration (This corresponds to 1.5 mg of docetaxel). To this wet mixture immediately 2 ml of a 5% aqueous dextrose solution are added and the mixture is shaken until a clear solution is obtained. The dissolved docetaxel concentration in solution according to Example I.5. amounts to 0.75 mg/ml. The solutions can be stored at room temperature under normal light conditions in glass containers for at least 24 hours without noticeable opalescence and/or particle formation. The composition of solutions referred to 20 mg docetaxel dosage unit is as follows:
2670 mg HPβCD
20 mg docetaxel
2 ml ethanol
27 ml 5% dextrose Example I.6.

Preparation of Binary paclitaxel/acetyl-γ-cyclodextrin co-lyophilisate 30 mg of paclitaxel dissolved in 3 ml of ethanol is added to 5.0 g of amorphised acetyl-γ-cyclodextrin. To the wet powder further 2 ml of ethanol are added and the powder is dissolved in 50 ml of distilled water resulting in a clear solution with 0.6 mg/ml nominal paclitaxel concentration. This solution is frozen quickly in dry-ice and freeze dried to obtain a white lyophilisate with 0.6±0.05%/w paclitaxel content.

This lyophilisate can easily be reconstituted into the original volume solution by way of adding of 50 ml of an 5% aqueous glucose solution. The result is a clear solution with 0.6 mg/ml paclitaxel concentration.

The reconstituted solution is stored at room temperature under normal conditions in glass containers. The paclitaxel concentration was assayed using the HPLC method after filtration of the test solutions through a 0.2 μm membrane. The paclitaxel content

| | |
|---|---|
| after preparation: | 0.513 ± 0.07 mg/mL* |
| after 25 hours of storage | 0.556 ± 0.01 mg/ml |

*The difference between nominal and measured paclitaxel concentration is due to the volume expansion of the bulk lyophilisate.

Example I.7.

Preparation of Binary docetaxel/acetyl-γ-cyclodextrin co-lyophilisate 10 mg of docetaxel dissolved in 0.5 ml of ethanol are added to 400 mg of amorphised acetyl-γ-cyclodextrin. The wet powder is dissolved in 8 ml of distilled water resulting in a clear solution with 1.25 mg/ml nominal docetaxel concentration. This solution is frozen quickly in dry-ice and freeze dried to obtain a white lyophilisate with 2.25±0.1% docetaxel content.

50 mg of the solid lyophilisate can easily be dissolved in 1 ml of a 5% aqueous glucose solution resulting in a clear solution of 1.13 mg/ml docetaxel content (determined by HPLC).

The reconstituted solution can be stored at room temperature under normal conditions in a glass container. After 21 hours of storage 1.15±0.02 mg/ml docetaxel concentration is assayed using the HPLC method. Even after 72 hours of storage there is no visually observable opalescence or solid particle formation in the solution.

Example I.8.

Preparation of paclitaxel/acetyl-γ-cyclodextrin/glucose co-lyophilisate 30 mg of paclitaxel are dissolved in 3 ml of ethanol and the solution is added to 5.0 g of amorphised acetyl-γ-cyclodextrin. To the wet powder further 2 ml of ethanol are added and the powder is then dissolved in 50 ml of a 5% aqueous glucose solution. This solution is frozen in dry-ice and freeze-dried to give a white lyophilisate with 0.42±0.01% paclitaxel content.

This lyophilisate can easily be reconstituted into the original volume on addition of 50 ml of distilled water. The result is a clear solution with 0.6 mg/ml nominal paclitaxel concentration.

The reconstituted solutions are stored at room temperature under normal conditions in closed glass containers. The paclitaxel concentration during storage is measured using the HPLC method after filtration of the test solutions.

Paclitaxel content found:

| | |
|---|---|
| immediately on preparation: | 0.530 ± 0.08 mg/mL* |
| after 25 hours of storage | 0.541 ± 0.05 mg/ml |

*The difference between nominal and measured paclitaxel concentration is due to the volume expansion of the bulk lyophilisate.

Example I.9.

Preparation of docetaxel/acetyl-γ-cyclodextrin/glucose co-lyophilisate 8 mg of docetaxel dissolved in 0.4 ml of ethanol are added to 400 mg of amorphised acetyl-γ-cyclodextrin. The wet powder is then dissolved in 8 ml of a 5% w/v aqueous glucose solution. This results in a clear solution with 1 mg/ml nominal docetaxel concentration which is frozen in dry-ice and freeze-dried, to give a white lyophilisate with 1% docetaxel content.

100 mg of ethanol free solid lyophilisate can easily be reconstituted in 1, 2 or 4 ml of distilled water giving clear solutions of 1, 0.5 or 0.25 mg/ml nominal docetaxel concentrations, respectively. In Table 6. physical stability of docetaxel solutions during 21 hours of storage at room temperature in closed glass containers are summarised by determination of the dissolved docetaxel concentration by HPLC at different nominal concentrations.

TABLE 6

| | Nominal dissolved docetaxel concentration | | |
|---|---|---|---|
| Dissolved docetaxel mg/ml HPLC | 1 mg/ml | 0.5 mg/ml | 0.25 mg/ml |
| at preparation | 0.93 | 0.49 | 0.24 |
| after 21 hours | 0.89 | 0.48 | 0.24 |

Example I.10.

Preparation of Binary docetaxel/hydroxypropyl-β-cyclodextrin (HPβCD) co-lyophilisate 6 mg of docetaxel dissolved in 0.3 ml of ethanol are added to 300 mg of HPβCD. The wet powder is dissolved in 6 ml of distilled water resulting in a clear solution with 1 mg/ml nominal docetaxel concentration. This solution is frozen quickly in dry-ice and freeze dried, to obtain a white lyophilisate with 2% w/w docetaxel content.

50 mg of the solid lyophilisate can easily be dissolved in 1 or 2 ml of a 5% w/v aqueous glucose solutions giving a clear solution of 0.97 and 0.59 mg/ml docetaxel content respectively, as determined by HPLC.

The reconstituted solutions are stored at room temperature under normal conditions in glass containers. After 21 hours of storage 0.95±0.05 and 0.49±0.005 mg/ml docetaxel concentrations are assayed by HPLC.

Example I.11

Prolongation of the Oversaturated Dissolved State of the paclitaxel by Way of Co-Evaporation 30 mg of Paclitaxel are dissolved in 6 ml of ethanol and the solution is mixed thoroughly with 5 g of acetyl-γ-cyclodextrin. Additional 3 ml of ethanol are added and the mixture is stirred for 5 minutes at room temperature. The ethanol content of the mixture is then removed in nitrogen stream using a rotatory evaporator in vacuum. The resulting white solid is then dissolved in 5 ml of deionised water resulting in a slightly opalescent solution that is immediately frozen with dry-ice and freeze-dried. The resulting lyophilisate is an instantly soluble amorphous powder. This is conveniently reconstituted to a clear solution by adding injectable water or a 5% aqueous glucose solution. The reconstituted solution with 0.3-0.6 mg/ml dissolved paclitaxel concentration remains stable for at least 24 hours at room temperature.

Example I.12

Parenteral Composition for Intravenous Use 100 mg of paclitaxel dissolved in 10 ml of ethanol are added to 15.0 g of amorphised large surface area acetyl-γ-cyclodextrin. To the wet powder further 10 ml of ethanol are added and the powder is dissolved in 80 ml of distilled water resulting in a clear solution with 1.25 mg/ml nominal paclitaxel concentration. This solution is frozen quickly in dry-ice and freeze-dried to yield a white lyophilisate with 0.7±0.05% w paclitaxel content.

This lyophilisate can easily be reconstituted to 100 ml using a 5% w/v aqueous dextrose solution. A clear solution with 1.0 mg/ml paclitaxel concentration is obtained ready to use for intravenous application.

II. Biological Studies

The aim of the studies was to evaluate some specific side effects of intravenous administration of paclitaxel. Cardiovascular and respiratory effects of paclitaxel following intravenous administration were examined on a total of 7 beagle dogs maintained under α-chloralose/sodium pentobarbitone anaesthesia.

II.1. Test Substances

A. Paclitaxel 1 ml liquid (30 mg/ml in ethanol) supplied in vials. Dissolved in vehicle Cremophor ELP:ethanol 1:1 on the course of the test.

B. Paclitaxel/AcγCD white crystalline powder; prepared according to Example I. I.6. of the present patent specification. Dissolved in vehicle 2.5% w/v aqueous dextrose on the course of the test.

II.2. Methods

The following parameters were recorded or derived and served as indicators of the functional status of the various elements within the cardiovascular and respiratory systems. The units of measurement are stated in parenthesis.

| | |
|---|---|
| Systolic, diastolic, mean blood pressure (mmHg) Heart rate (beats/minute) | General haemodynamic status |
| Left ventricular systolic pressure (mmHg) Left ventricular dp/dt max. (mmHG. sec$^{-1}$) | Contractile status of the myocardium |
| Electrodiagram (lead H) | Electrical status of the myocardium |
| Femoral flow (ml/minute) Femoral resistance (mmHg/ml/minute) | Status and resistance of the peripheral vasculature |
| Respiration rate (breaths/minute) Respiration minute volume (ml) Respiration tidal volume (ml) | General respiratory status |

Anaesthesia was induced by i.v. injection of sodium thiopentone and maintained i.v. by a mixture of α-chloralose and pentobarbitone sodium given as required. Body temperature was maintained.

The trachea was cannulated and the canule connected to a pneumotach screen to allow measurement of tidal volume (ml) and the derived parameters of respiration rate (br/min) and minute volume (ml). Catheters were introduced into the right femoral artery and a cephalic vein to facilitate measurements of blood pressure and the administration of vehicle, test substances and anaesthetic respectively. The femoral artery was connected to a heparin/saline filled pressure transducer, coupled to a Grass 7E polygraph. Heart rate was derived electronically from the blood pressure signal.

An ultrasonic flow probe was positioned around the left femoral artery and connected to a blood flow meter coupled to the Grass polygraph to record femoral blood flow (ml/min).

A catheter was introduced into the left carotid artery and advanced into the left ventricle to facilitate the measurement of the left ventricular systolic pressure (LVSP). The catheter was connected to a heparin/saline-filled pressure transducer and the LVSP signal was displayed on the Grass polygraph.

Subcutaneous needle electrodes were inserted in the appropriate limbs in order to monitor the electrocardiogram which was displayed on the Grass polygraph. Various signals were transferred from the Grass polygraph to a computer and the captured data were analysed and displayed.

Following a 30 minute stabilization period, the vehicle was administered i.v. at a dose volume of 7.0 ml/kG over a period of 15 minutes. 45 minutes later and a minimum of 45 minutes intervals thereafter doses of the drugs were administered i.v. at a dose volume of 7.0 ml/kG again over 15 minutes each. The parameters were monitored for a least 45 minutes from the start of infusion. All doses were administered using a KdS model 200 infusion pump.

Following samples were tested:

| N° | Animal | Vehicle i.v. 7 ml/kG, 15 min. | Drug | Drug Dose mg/m$^2$ |
|---|---|---|---|---|
| 1. | | Cremophor ELP: ethanol | paclitaxel | 6; 60 |
| 2. | | Cremophor ELP: ethanol | paclitaxel | 6; 60 |
| 3. | 2901AK | Cremophor ELP: ethanol | none | — |
| 4. | 2841AK | Cremophor ELP: ethanol | none | — |
| 5. | D2515 | 2.5% dextrose/in water | paclitaxel/ AcγCD* | 10; 20; 40; 60 |
| 6. | D2937 | 2.5% dextrose/in water | paclitaxel/ AcγCD* | 40, 10, 60, 90 |
| 7. | D5 | 2.5% dextrose/in water | paclitaxel/ AcγCD* | 90; 120; 240 |

*= prepared according to Example I.6.

All parameters including high resolution (50 mm/sec) recordings of the ECG were measured at 5 minute intervals during the stabilization period and at 0.5, 1, 2 and 5 minutes intervals post-dose following vehicle and drug administration. At the end of the full observation period the animals were killed with and overdose of pentobarbitone sodium, i.v.

II.3. Results

Animals Results 1 and 2 Administration of 6 and 60 mg/m$^2$ paclitaxel in Cremophor ELP:ethanol 1:1 was discontinued because of death of the animals.

3 and 4 Intravenous administration of Cremophor ELP:ethanol at both dose levels (corresponding to the doses used with 6 and 60 mg/m$^2$ paclitaxel respectively) induced an anaphylactic type response: immediate decrease in arterial blood pressure, heart rate, left ventricular systolic pressure and left ventricular dp/dt maximum of similar magnitude in both animals. Little or no recovery in any cardiovascular parameter was observed post-dose. Both doses levels induced ventricular ectopic beats, reduced the overall amplitude of the ECG wave-form, caused notching of the T-wave and reduction in T-wave amplitude. In animal 2841AK the vehicle also induced elevation of the S-T segment.

As a results of these finding it may be concluded that the solvent-mixture per se is toxic and should be avoided in i.v. administration.

5; 6; 7 Administration of 2.5% w/v of dextrose at a dose volume of 7 ml/kG induced no overall overt effects on any of the cardiovascular or respiratory parameters in the 3 animals tested. Addition of the paclitaxel/AcγCD doses up to 240 mg/m2 in general caused only small changes in the measured cardiovascular and respiratory parameters. Slight effects included slight increases in arterial blood pressure and left ventricular systolic pressure, accompanied by decreases in heart rate and left ventricular dp/dt maximum. Other inconsistent changes included increases in femoral flow, tidal volume and respiration rate. The findings were reversible.

II.4. Figures

Figure 1:
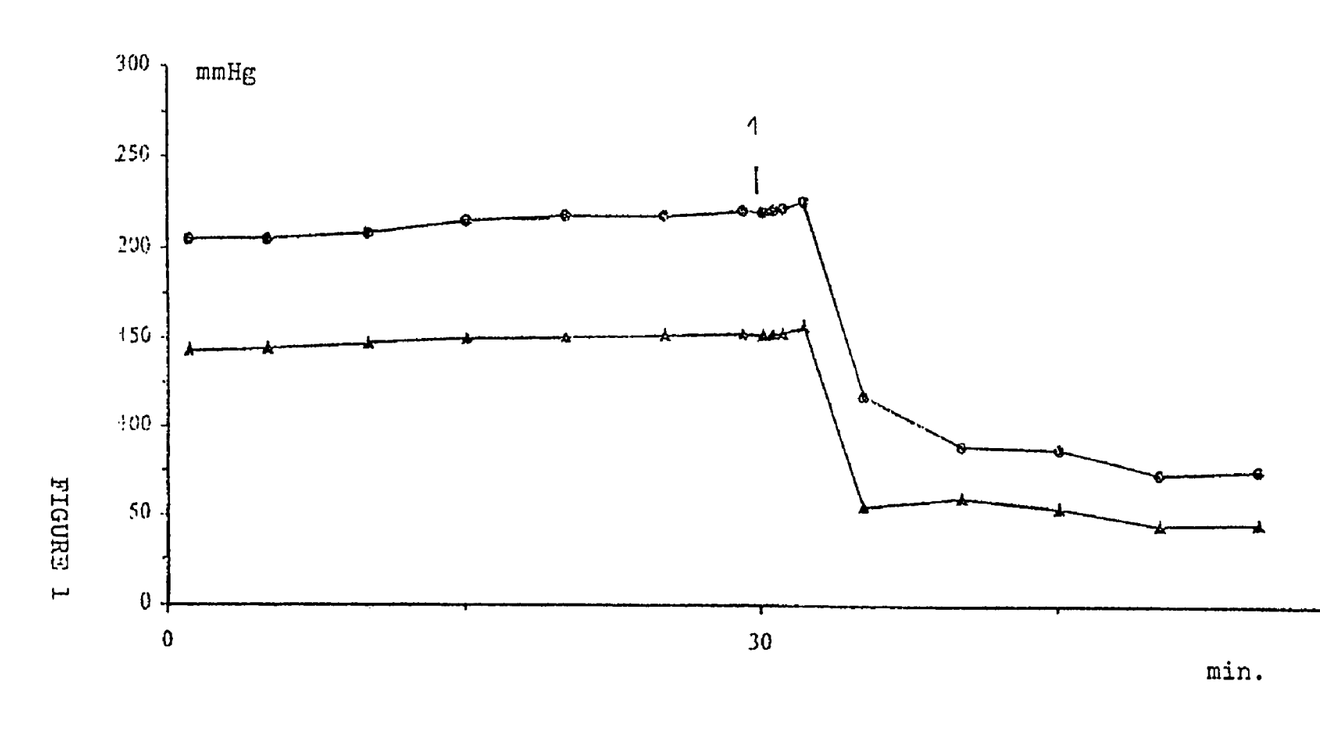
FIG. 1 is arterial blood pressure (mmHg) versus time (minutes) graph of the results following i.v. administration in the anaesthetised beagle dog (2901AK) of Cremophor:ethanol vehicle.
Figure 2:
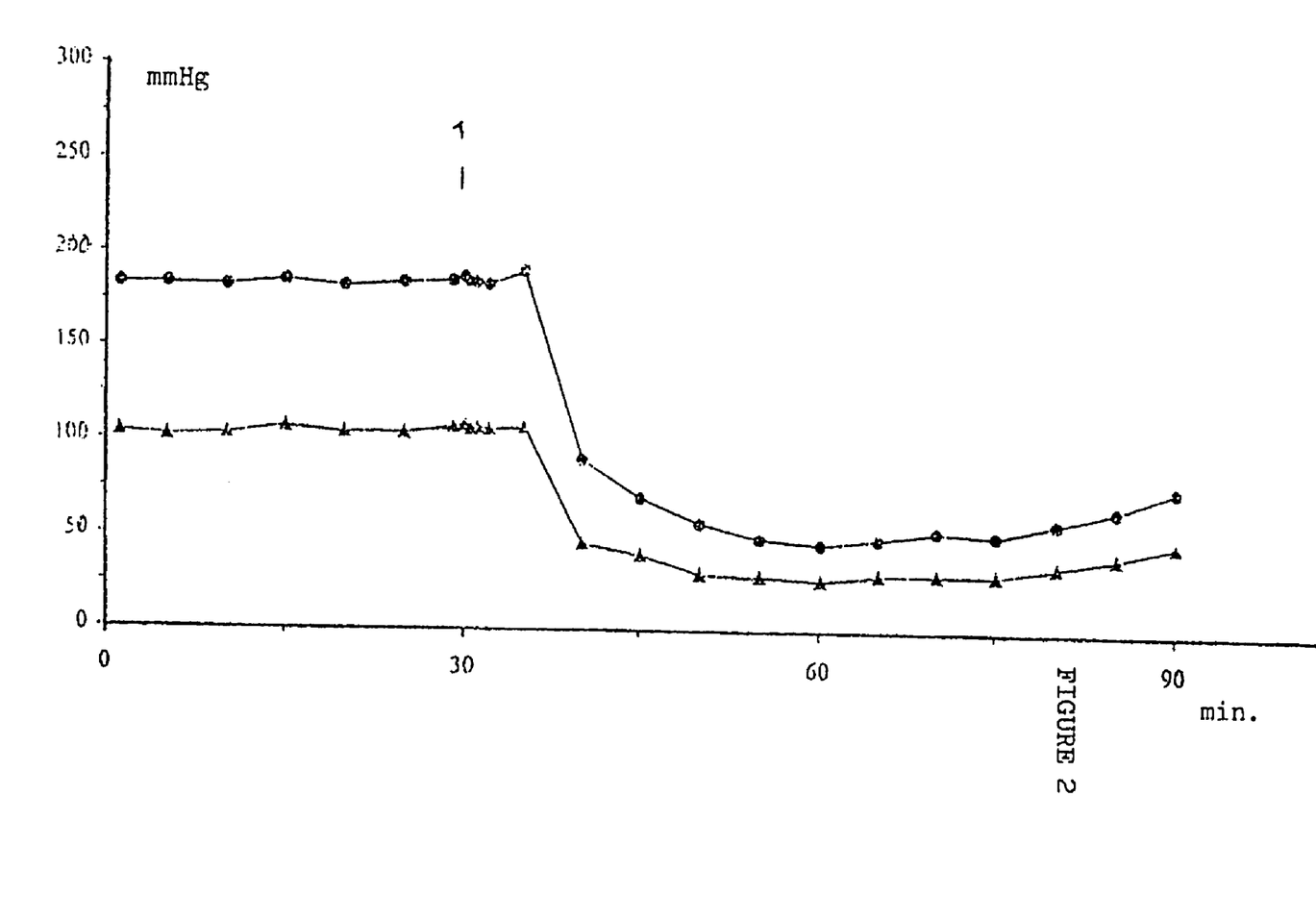
FIG. 2 is arterial blood pressure (mmHg) versus time (minutes) graph of the results following i.v. administration in the anaesthetised beagle dog (2841AK) of Cremophor:ethanol vehicle.
Figure 3:
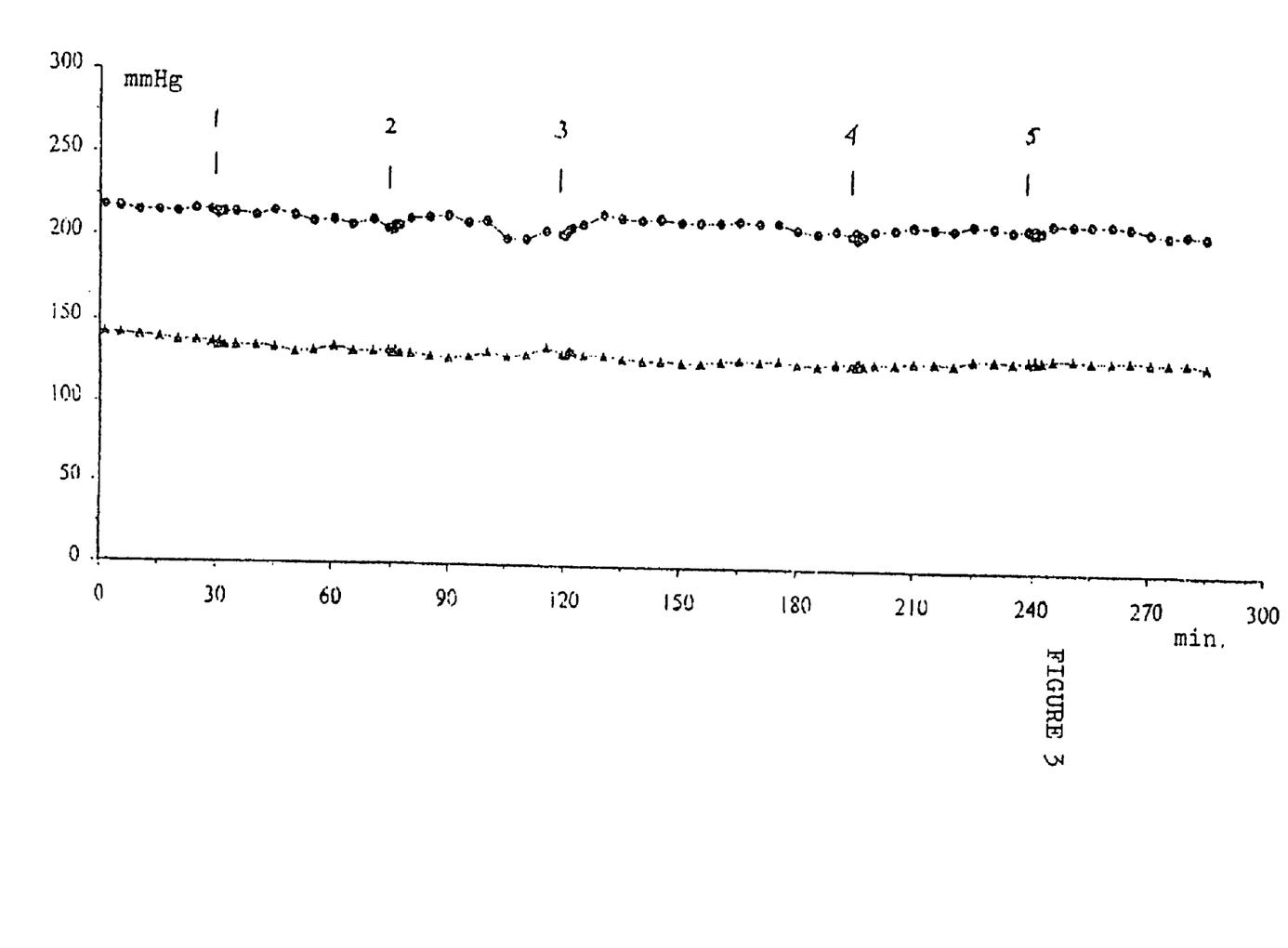
FIG. 3 is arterial blood pressure (mmHg) versus time (minutes) graph of the results following i.v. administration in the anaesthetised beagle dog (D2515) of paclitaxel/AcγCD Ex. I.6. 10, 20, 40, 60 mg/m$^2$ in 2.5% dextrose in water vehicle.
Figure 4:
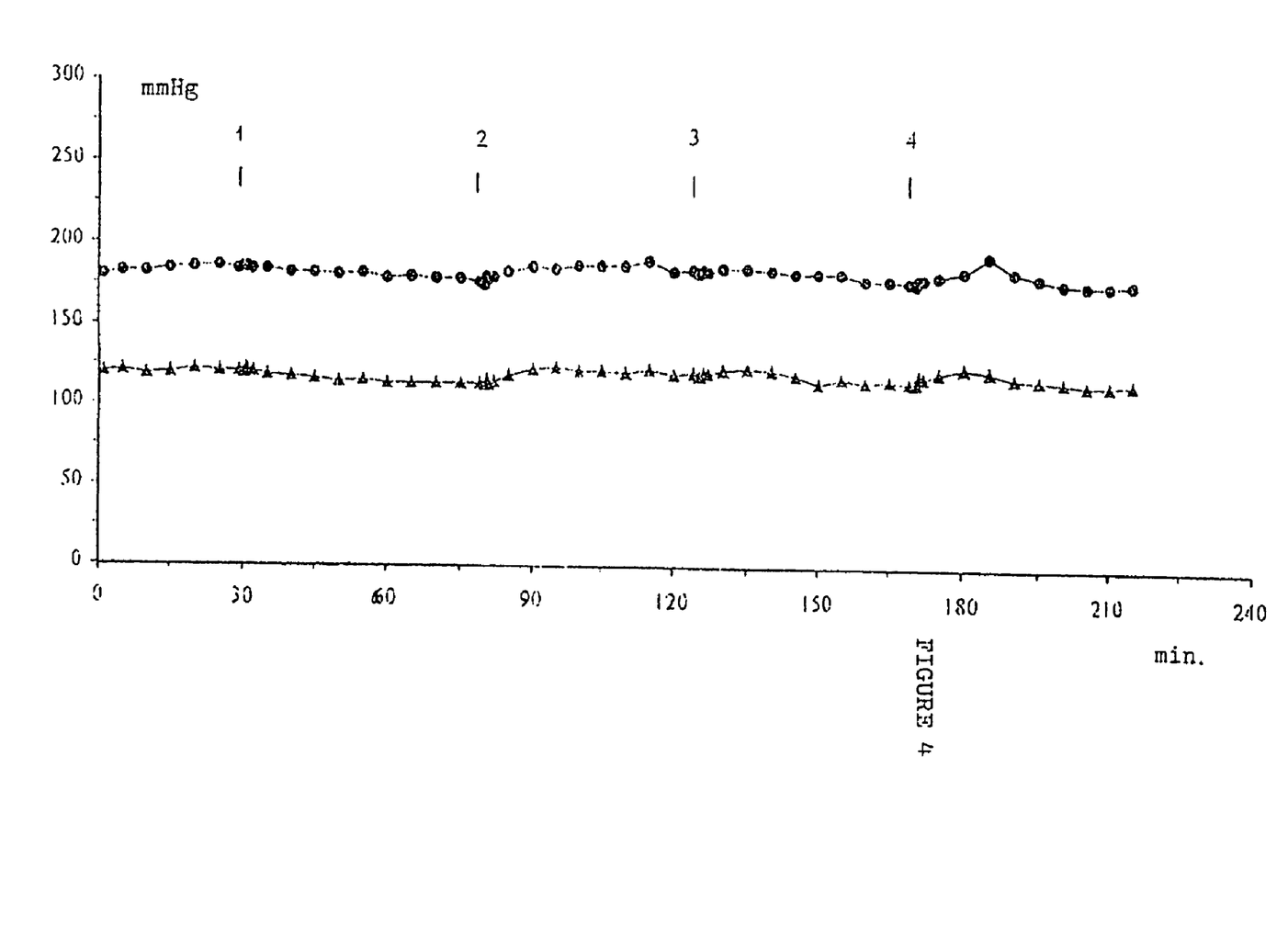
FIG. 4 is arterial blood pressure (mmHg) versus time (minutes) graph of the results following i.v. administration in the anaesthetised beagle dog (D5) of paclitaxel/AcγCD Ex. I.6. 120, 90, 240 mg/m$^2$ in 2.5% dextrose in water vehicle.
Figure 5:
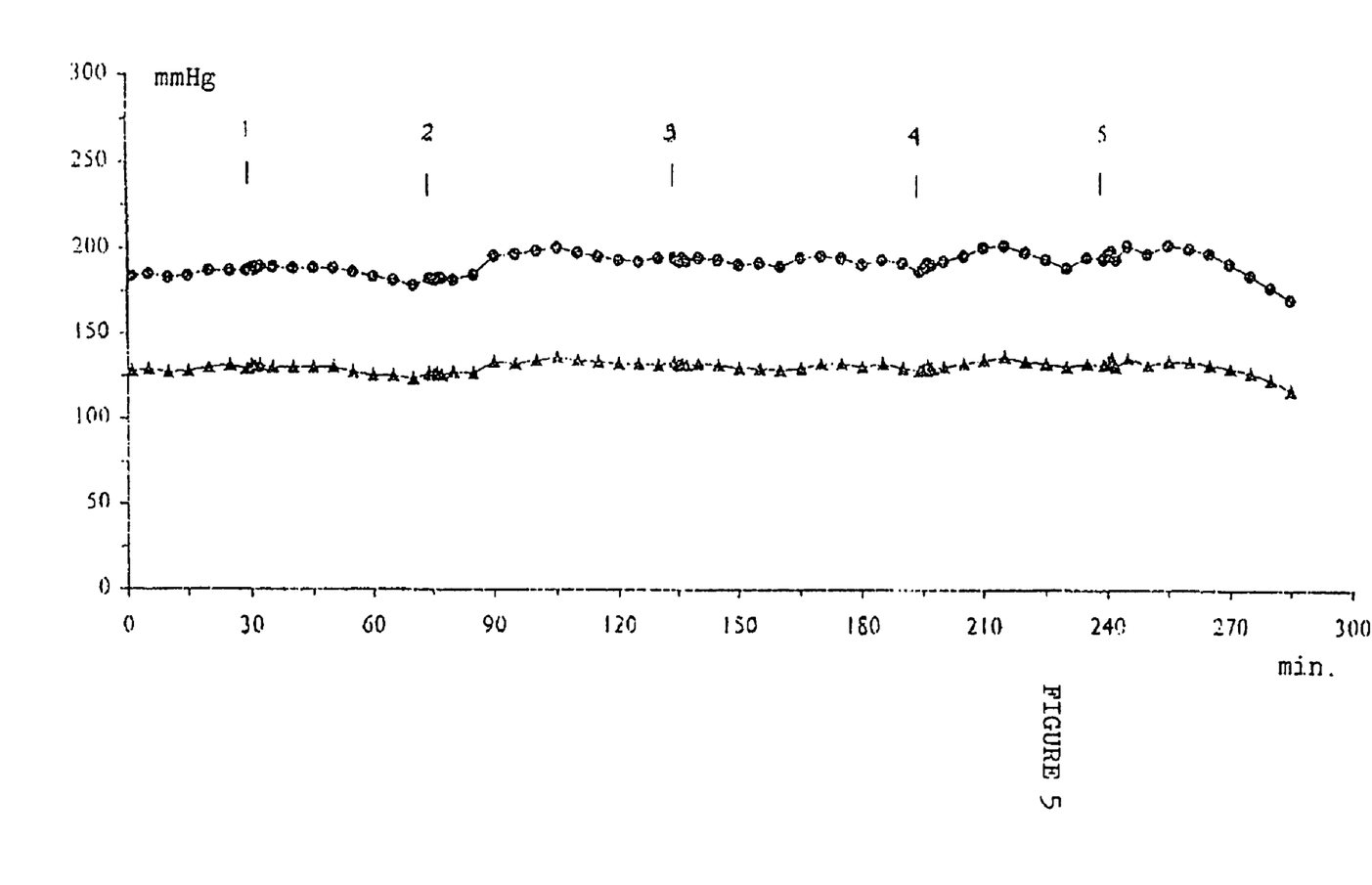
FIG. 5 is arterial blood pressure (mmHg) versus time (minutes) graph of the results following i.v. administration in the anaesthetised beagle dog (D2937) of paclitaxel/AcγCD Ex. I.6. 10, 90, 40, 60 mg/m$^2$ in 2.5% dextrose in water vehicle.
Figure 6:
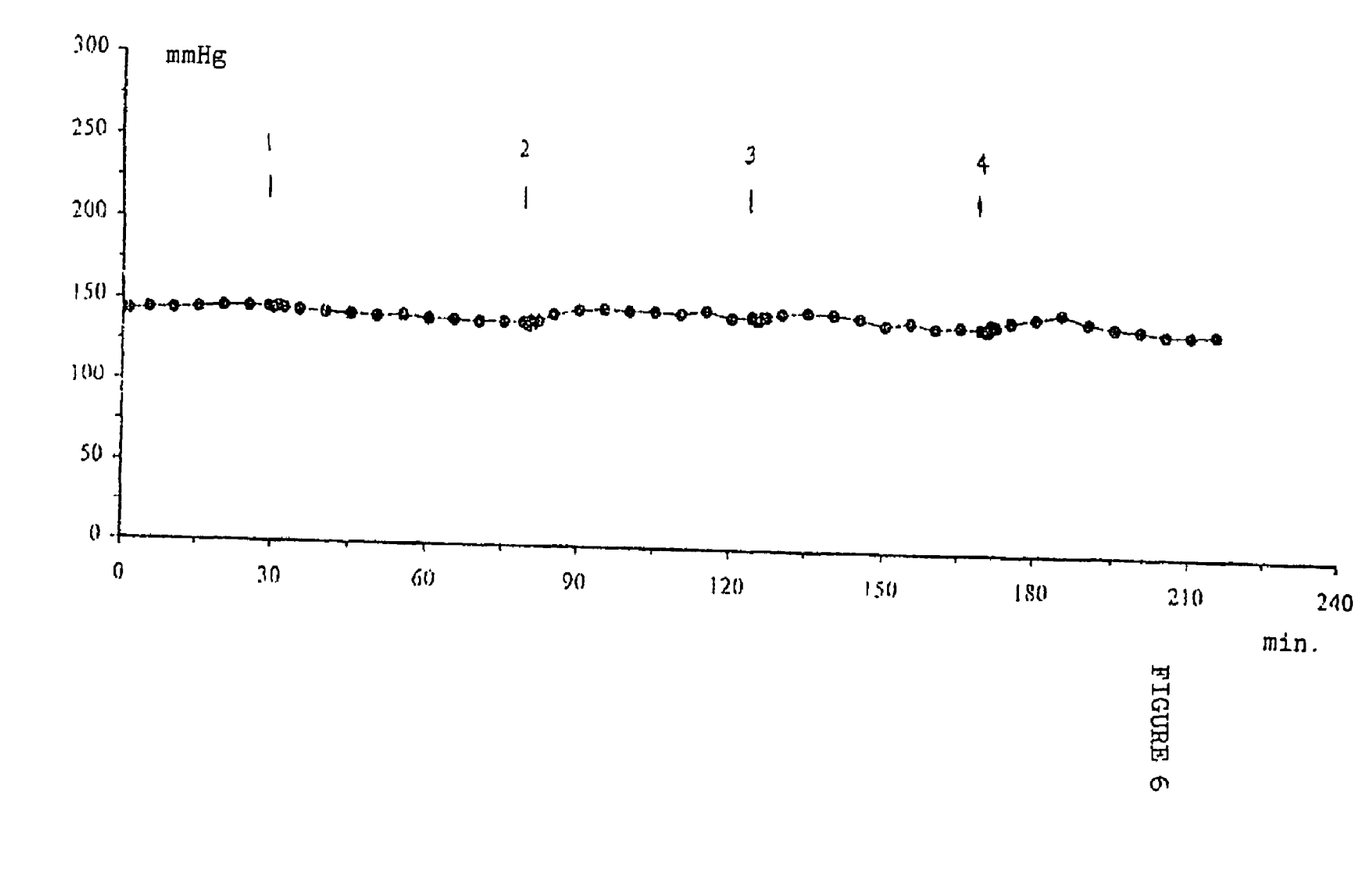
FIG. 6 is mean arterial blood pressure (mmHg) versus time (minutes) graph of the results following i.v. administration in the anaesthetised beagle dog (D5) of paclitaxel/AcγCD Ex. I.6. 120, 90, 240 mg/m$^2$ in 2.5% dextrose in water vehicle.

To illustrate an important parameter of the results the effect on arterial blood pressure following i.v. administration in the anaesthetised beagle dog is shown in FIGS. 1 to 6:

Arterial blood pressure (mmHg) versus time (minutes):

| Graph | animal | vehicle | drug mg/m² |
|---|---|---|---|
| FIG. 1 | 2901AK | Cremophor: ethanol | none |
| FIG. 2 | 2841AK | Cremophor: ethanol | none |
| FIG. 3 | D2515 | 2.5% dextrose in water | paclitaxel/AcγCD Ex. I. 6. 10, 20, 40, 60 |
| FIG. 4 | D5 | 2.5% dextrose in water | paclitaxel/AcγCD Ex. I. 6. 120, 90, 240 |
| FIG. 5 | D2937 | 2.5% dextrose in water | paclitaxel/AcγCD Ex. I. 6. 10, 90; 40; 60 |
| FIG. 6 mean pressure | D5 | 2.5% dextrose in water | paclitaxel/AcγCD Ex. I. 6. 120; 90; 240 |

II.5. Summary

Intravenous administration of the Cremophor ELP:ethanol 1:1 vehicle as well as paclitaxel along with this vehicle caused an anaphylactic type reaction and is thus inadequate to be administered. Administration of paclitaxel/acetyl-γ-CD (from 20 mg up to 240 mg/m²) in aqueous dextrose as vehicle failed to produce marked and persistent cardiovascular overt effects on any of the parameters in any of the animals tested.

The invention claimed is:

1. A process for the preparation of instantly soluble solid products for pharmaceutical parenteral comprising:
   (a) dissolving in ethanol a taxoid selected from the group consisting of paclitaxel or a salt or hydrate thereof and docetaxel, or a salt or hydrate thereof, to form a solution and thereafter,
   (b) adding to the solution a lyophilized solid cyclodextrin derivative selected from the group consisting of acetyl-γ-cyclodextrin having a degree of acetylation between about 2 to about 12 acetyl groups per cyclodextrin ring and hydroxyl-propyl-β-cyclodextrin having a degree of substitution between about 2 to about 12 hydroxypropyl groups per cyclodextrin ring,
   (c) evaporating the solvent and drying to obtain an instant soluble solid,
   (d) dissolving said solid in an aqueous solvent selected from the group consisting of water, aqueous glucose and aqueous dextrose, thus obtaining an aqueous solution, and
   (e) freezing the solution and lyophilising it to obtain an instantly soluble lyophilisate including
      A. as an active ingredient the said taxoid and
      B. the said cyclodextrin derivative whereby the weight ratio of taxoid:cyclodextrin ranges between 1:25 and 1:400;
   with the restriction that when hydroxyl-propyl-β-cyclodextrin is used the taxoid can be only docetaxel in a 1:25 to 1:100 taxoid:cyclodextrin weight ratio.

2. A process for the preparation of solutions in aqueous solvents of instantly soluble solid products for pharmaceutical parenteral comprising:
   (a) dissolving in ethanol a taxoid selected from the group consisting of paclitaxel or a salt or hydrate thereof and docetaxel, or a salt or hydrate thereof to form a solution; and thereafter,
   (b) adding to the solution a lyophilized solid cyclodextrin derivative selected from the group consisting of acetyl-γ-cyclodextrin having a degree of acetylation between about 2 to about 12 acetyl groups per cyclodextrin ring and hydroxyl-propyl-β-cyclodextrin having a degree of substitution between about 2 to about 12 hydroxypropyl groups per cyclodextrin ring, and
   (c) evaporating the solvent and drying to obtain a solid; and
   (d) dissolving said solid in an aqueous solvent selected from the group consisting of water, aqueous glucose and aqueous dextrose, thus obtaining an aqueous solution;
   (e) freezing the aqueous solution and lyophilising it to obtain an instantly soluble lyophilisate; and
   (f) redissolving the lyophilisate in an aqueous solvent selected from the group consisting of water, aqueous glucose and aqueous dextrose, thus obtaining an aqueous solution including
      A. as an active ingredient the said taxoid and
      B. the said cyclodextrin derivative;
   whereby the weight ratio of taxoid:cyclodextrin ranges between 1:25 and 1:400;
   with the restriction that when hydroxyl-propyl-β-cyclodextrin is used the taxoid can be only docetaxel in a 1:25 to 1:100 taxoid:cyclodextrin weight ratio.

3. The process according to claim 2, wherein the aqueous solvent is selected from the group consisting of water of injectiable quality and an aqueous solution of isotonizing additive in an effective amount to isotonize the aqueous solution.

4. The process according to claim 1 wherein the acetyl-γ-cyclodextrin has a degree of acetylation of about 8 acetyl groups per cyclodextrin ring.

5. The process according to claim 2 wherein the acetyl-γ-cyclodextrin has a degree of acetylation of about 8 acetyl groups per cyclodextrin ring.

6. The process according to claim 1 wherein said paclitaxel is in its hydrated polymorphic form.

7. A process for the preparation of solutions in aqueous solvents of instantly soluble solid products for pharmaceutical parenteral comprising:
   (a) dissolving a paclitaxel salt or hydrate thereof in ethanol, to form a solution, and thereafter
   (b) adding to the solution a lyophilized solid acetyl-γ-cyclodextrin having a degree of acetylation between about 2 to about 12 acetyl groups per cyclodextrin ring; and
   (c) evaporating the solvent and drying to obtain a solid; and
   (d) dissolving said solid in water thus obtaining an aqueous solution;
   (e) freezing the aqueous solution and lyophilising it to obtain an instantly soluble lyophilisate; and
   (f) redissolving the lyophilisate in an aqueous solvent selected from the group consisting of water or aqueous glucose, thus obtaining an aqueous solution including
      A. as an active ingredient the said taxoid and
      B. the said acetyl-γ-cyclodextrin;
   whereby the weight ratio of paclitaxel:acetyl-γ-cyclodextrin ranges between 1:25 and 1:400.

* * * * *